(12) United States Patent
Dunshee

(10) Patent No.: US 7,066,182 B1
(45) Date of Patent: Jun. 27, 2006

(54) CONFORMABLE ADHESIVE WOUND CLOSURES

(75) Inventor: Wayne K. Dunshee, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 946 days.

(21) Appl. No.: 09/671,129

(22) Filed: Sep. 27, 2000

(51) Int. Cl.
*A61F 13/00* (2006.01)

(52) U.S. Cl. .......................................... 128/888; 602/41
(58) Field of Classification Search ................. 128/888, 128/889; 602/41–59
See application file for complete search history.

(56) References Cited

U.S. PATENT DOCUMENTS

| | | | |
|---|---|---|---|
| RE24,906 E | | 12/1960 | Ulrich |
| 3,665,918 A | | 5/1972 | Lindquist et al. |
| 3,677,250 A | | 7/1972 | Thomas |
| 4,141,363 A | * | 2/1979 | James ........................ 128/335 |
| 4,302,500 A | | 11/1981 | Flora |
| 4,472,480 A | | 9/1984 | Olson |
| 4,605,005 A | | 8/1986 | Sheehan |
| 4,612,230 A | | 9/1986 | Liland et al. |
| 4,702,251 A | | 10/1987 | Sheehan |
| 4,780,168 A | | 10/1988 | Beisang et al. |
| 4,815,468 A | | 3/1989 | Annand |
| 4,825,866 A | | 5/1989 | Pierce |

(Continued)

FOREIGN PATENT DOCUMENTS

| | | |
|---|---|---|
| EP | 831401 | 3/1960 |
| EP | 0 676 183 A1 | 11/1995 |
| GB | 2 251 796 | 7/1992 |
| WO | WO 92/10983 | 7/1992 |
| WO | WO 93/17633 | 9/1993 |
| WO | WO 00/49983 | 8/2000 |

OTHER PUBLICATIONS

Johnson and Johnson® Brand Butterfly Closures, Sterile waterproof closures for small wounds and incisions, Medium closures 1¾ in. × ⅜ in. (4.5cm ×1cm), Johnson and Johnson Consumer Products Company, Skillman, NJ, 2 pgs (1995).
BAND–AID Brand Adhesive Bandages Product Sheet for "Butterfly Closures," Johnson & Johnson Gateway LLC (online, retrieved Feb. 27, 2001 from the Internet:<URL: http://www.jnjgateway.com/gateway_global/user/gateway. cfm?jnj gateway=family&familyid=676&spec=1&locale= 10>), 3 pages.

(Continued)

*Primary Examiner*—Michael A. Brown
(74) *Attorney, Agent, or Firm*—Nancy M. Lambert

(57) ABSTRACT

A wound closure including a wound bridging portion that has sufficient dimensional stability to hold the wound edges in proper alignment, even in the face of substantial stretching of the wound closure as a whole, is disclosed. The wound closure is dimensionally stable directly over the wound. The remainder of the wound closure is preferably substantially more extensible and elastic than the wound bridging portion to improve conformability and adhesion of the wound closure to the patient. The wound closures may include opposing end portions of unequal lengths yielding an asymmetric shape that facilitates close placement of the wound closures along a wound.

30 Claims, 4 Drawing Sheets

U.S. PATENT DOCUMENTS

| | | |
|---|---|---|
| 4,950,282 A | 8/1990 | Beisang et al. |
| 4,995,114 A | 2/1991 | Price, Jr. |
| 5,176,703 A | 1/1993 | Peterson |
| 5,230,701 A | 7/1993 | Meyer et al. |
| 5,259,835 A | 11/1993 | Clark et al. |
| 5,377,695 A | 1/1995 | An Haack |
| 5,445,597 A | 8/1995 | Clark et al. |
| 5,497,788 A | 3/1996 | Inman et al. |
| D371,604 S | 7/1996 | Savage et al. |
| 5,531,855 A | 7/1996 | Heinecke et al. |
| 5,534,010 A | 7/1996 | Peterson |
| 5,538,500 A | 7/1996 | Peterson |
| 5,630,430 A | 5/1997 | Shultz et al. |
| D385,038 S | 10/1997 | Shultz |
| 6,107,219 A | 8/2000 | Joseph et al. |
| 2001/0037077 A1 * | 11/2001 | Wiemken .................... 602/41 |

OTHER PUBLICATIONS

3M™ Steri–Strip™ Elastic Skin Closures "Conformable closures even in the toughest places," product literature, 3M Health Care, St. Paul, Minnesota, 2 pgs. (1997).

3M™ Steri–Strip™ Adhesive Skin Closures "Quality plus versatility . . . Because one size does not fit all," product literature, 3M Health Care, St. Paul, Minnesota, 9 pgs. (1994).

* cited by examiner

CONFORMABLE ADHESIVE WOUND CLOSURES

TECHNICAL FIELD

The invention relates generally to adhesive wound closures.

BACKGROUND

In medicine, sutures have long been used to close serious wounds. More recently, adhesive closures have been introduced that can effectively close some types of wounds without inflicting the additional injury inherent in suturing. These adhesive closures have a backing to provide solid structure, and have an adhesive layer for adhering to the skin. There are two main criteria that must be reconciled in a successful design for these products: reliable adhesion to the skin, even when the wound is adjacent to a joint; and good performance in keeping the wound edges in proximity to each other.

One approach is to use a non-woven web as the basic backing, and to reinforce this material with strong fibers in the longitudinal, or cross-wound, direction. The main substance of the backing can bend with the skin as the patient moves, and the reinforcing fibers strengthen the lightweight backing so that the structure can resist wound edge separation. This backing is combined with a strong skin adhesive over the entire skin contacting surface. The strength of the reinforcing fibers, combined with their secure anchorage immediately adjacent to the wound edges provides excellent security against wound separation. For example, Steri-Strips™ wound closures, commercially available from Minnesota Mining and Manufacturing Company of St. Paul, Minn., are constructed in this way.

One limitation on this approach is partially a psychological one, i.e., concern about the placement of skin adhesive to the area directly above the wound edge. That concern may include an apprehension that the adhesive will stick to the wound edge and re-open the partially healed wound when the closure is removed at the end of treatment. This can, in fact, happen if care is not taken when removing the closures.

To address the problem of adhesion to wound edges, some wound closures include a non-adhesive wound contact layer adhered to the skin adhesive layer over a limited surface area of the underside of the skin adhesive layer, so as to be placed right over the wound. Because such devices are not anchored immediately adjacent the wound edges, the desired dimensional stability to resist wound opening is provided primarily by the backing. For example, Band-Aid Brand Butterfly Closures, commercially available from Johnson & Johnson Company of Skillman, N.J., are constructed in this way. Because the backing is substantially stiff overall, however, it can be difficult to obtain good long-term adhesion adjacent to a joint where, for example, the skin is constantly stretching and unstretching.

Reconciling these approaches to obtain good conformability and adhesion, secure wound edge positioning, and easy release of the product from the wound edge at the end of treatment, would be much appreciated by medical practitioners. Additionally, it would be appreciated if such a wound closure were constructed so as to fit more easily onto body locations were space is at a premium. Cuts to the face over the bony ridge just above the eye, for example, are difficult to treat with existing products since their length carries them onto the eyelid.

SUMMARY OF THE INVENTION

The present invention addresses the problems discussed above by providing a wound closure including a wound bridging portion that has sufficient dimensional stability to hold the wound edges in proper alignment, even in the face of substantial stretching of the wound closure as a whole. The wound bridging portion is dimensionally stable where it is most needed, i.e., directly over the wound. The remainder of the wound closure is preferably substantially more extensible and elastic than the wound bridging portion to improve conformability and adhesion of the wound closure to the patient.

The invention preferably provides a wound closure having a backing made from an elastomeric web, preferably a nonwoven elastomeric web including thermoplastic elastomeric melt blown fibers. The backing material preferably has multi-directional elastic properties, so much so that the wound closure recovers at least 85% after being stretched 30%. More preferably, the backing recovers at least 95% after being stretched 30%.

The wound bridging portion is relatively dimensionally stable, i.e., the wound bridging portion stretches less than the remainder of the wound closure, e.g., the opposing end portions, when the wound closure is subjected to a stretching force. The wound bridging portion preferably stretches 8% or less when the wound closure stretches 30%. More preferably, the wound bridging portion stretches 5% or less when the wound closure stretches 30%, and most preferably the wound bridging portion stretches 1% or less when the wound closure stretches 30%. In some instances, the wound bridging portion may experience some elongation, i.e., stretches more than 0%, when the wound closure is stretched.

A reinforcing layer that is separate from a backing may be used in the wound bridging portion of the wound closure to provide the desired dimensional stability to the wound bridging portion. That reinforcing layer may take the form of a wound contact layer (i.e., a layer in contact with a wound when in use) if it is located on the patient side of the wound closure. Alternatively, for example, the reinforcing layer may be located on the side of the backing facing away from the wound. Regardless of its location, it is preferred that the reinforcing layer be firmly attached to the backing such that the reinforcing layer does not delaminate from the wound closure when the wound closure stretches, more preferably, the reinforcing layer does not delaminate from the wound closure when the wound closure stretches 30%. The reinforcing layer may be attached to the wound closure using any suitable technique, e.g., adhesives, welding, etc.

If the reinforcing layer is located on the wound side of the wound closure, it may be preferred that the reinforcing layer have a thickness of 75 microns (0.003 inch) or less. Thicker layers may be detectable because the patient can sometimes feel the reinforcing wound contact layer against the tender wound edges. More preferably, the wound contact layer has a thickness of 60 microns (0.0023 inch) or less.

The wound closures of the invention also include adhesive for attaching the wound closure to the skin. The adhesive is preferably a pressure sensitive adhesive. Preferably, this is a relatively aggressive adhesive, capable of taking a firm grip on the patient's skin to prevent unwanted detachment. The adhesive used to attach the wound closure to the patient's skin may also be used to attach a reinforcing layer to the wound closure in the wound bridging portion if that adhesive is strong enough to prevent delamination of the reinforcing layer from the wound closure when the wound closure stretches.

In one aspect, the present invention provides a wound closure for closing a wound in skin, the wound closure including an adhesive for adhering the wound closure to skin; opposing elastomeric end portions; and a wound bridging portion between the end portions; wherein the wound closure recovers at least 85% after being stretched 30%, and wherein the wound bridging portion stretches less than the end portions when subjected to the same force, whereby the wound bridging portion tends to maintain the wound closed against forces generated by stretching of skin.

In another aspect, the present invention provides a wound closure for closing a wound in skin, the wound closure including opposing end portions and an intermediate portion separating the end portions; an adhesive for adhering the wound closure to skin; wherein the end portions and the intermediate portion include an elastomeric backing; and wherein a reinforcing layer is attached to the backing only in the intermediate portion such that the intermediate portion defines a wound bridging portion including the elastomeric backing and the reinforcing layer; and further wherein the wound closure recovers at least 85% after being stretched 30% and the wound bridging portion stretches less than the end portions when subjected to the same force, whereby the wound bridging portion tends to maintain the wound closed against forces generated by stretching of skin.

In another aspect, the present invention provides a wound closure for closing a wound in skin, the wound closure including an adhesive for adhering the wound closure to skin; two opposing end portions located at opposing ends along a length of the wound closure; and a wound bridging portion separating the opposing end portions, the wound bridging portion having a width less than a width of the end portions; wherein the opposing end portions have unequal lengths as measured from the wound bridging portion to the ends of the wound closure.

In another aspect, the present invention provides a method of tending a wound by providing a wound closure having a short side and a long side, the wound closure including an adhesive for adhering the wound closure to skin; two opposing end portions located at opposing ends along a length of the wound closure; and a wound bridging portion separating the opposing end portions, the wound bridging portion having a width less than a width of the end portions. The opposing end portions of the wound closure have unequal lengths as measured from the wound bridging portion to the ends of the wound closure, with the shorter end portion providing the short side of the wound closure and the longer end portion providing the long side of the wound closure. The method further includes adhering the wound closure to a patient such that the wound bridging portion spans a wound.

These and other features and advantages of the present invention are discussed in connection with illustrative embodiments of the invention below.

BRIEF DESCRIPTION OF THE DRAWING

In the several figures of the attached drawing, like parts bear like reference numerals, and.

DETAILED DESCRIPTION OF ILLUSTRATIVE EMBODIMENTS OF THE INVENTION

Figure 1:
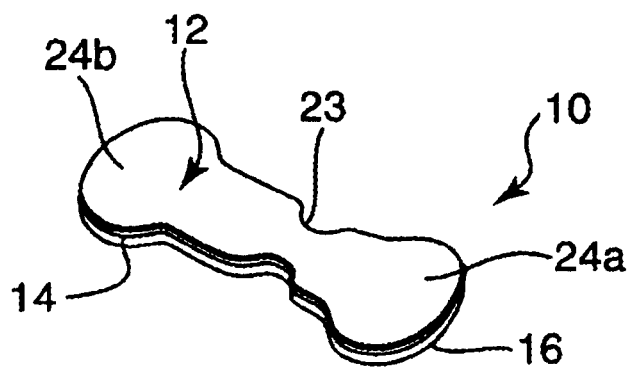
FIG. 1 illustrates a perspective view of a wound closure made according to the present invention.
Figure 2:
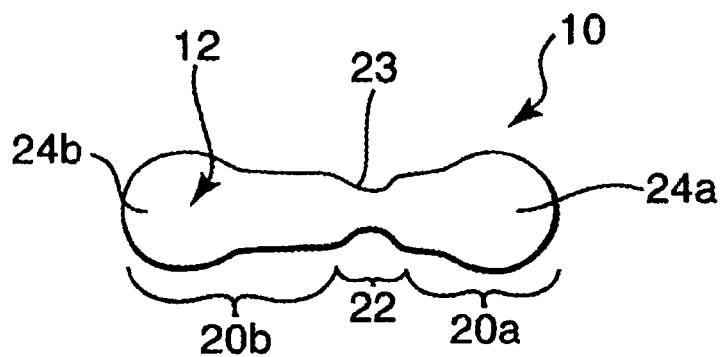
FIG. 2 illustrates a top plan view of the wound closure in FIG. 1.

Referring now to FIGS. 1 and 2, an exemplary wound closure 10 according to the present invention is illustrated. The wound closure 10 has a backing 12 and a layer of skin adhesive 14 contacting the backing. The depicted embodiment conveniently includes a release liner 16 to protect the adhesive layer 14 between the time the wound closure 10 is made and the time when it is to be applied to the skin.

The wound closure 10 includes a wound bridging portion 22 located between opposing end portions 20a and 20b. The wound bridging portion 22 preferably includes a neck 23 where the width narrows as compared to the opposing end portions 20a and 20b (where width is measured transverse to the length of the wound closure 10). The neck 23 of the wound bridging portion 22 is intended to be placed directly over the wound edges on the body so that the maximum practical amount of the wound can be seen by medical practitioners.

Pad portions 24a and 24b are preferably located at the distal ends of the end portions 20a and 20b of the wound closure 10. The pad portions 24a and 24b may widen as illustrated to increase the surface area available for the adhesive layer 14 to take an adhesive purchase on the skin's surface.

Referring to FIG. 2, it may be preferred that the wound closure 10 is not symmetrical from end to end, but rather the lengths of the opposing end portions 20a and 20b as measured from the wound bridging portion 22 are unequal, i.e., one of the end portions 20a is shorter than end portion 20b. The benefits of such an asymmetrical arrangement are discussed in greater detail below.

Figure 3:
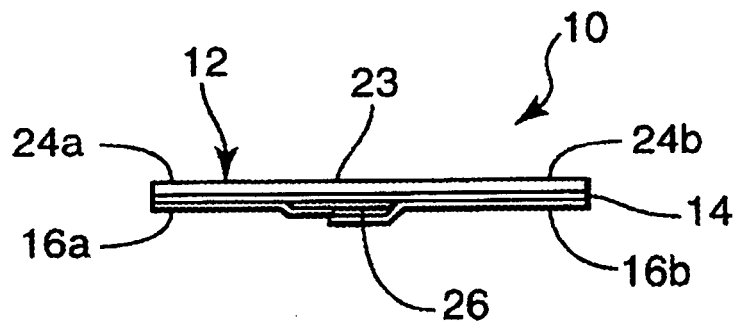
FIG. 3 illustrates a side view of the wound closure of FIG. 2.

A side view of the wound closure of FIG. 2 is depicted in FIG. 3. In this view it may be seen that the release liner 16 may conveniently be divided into two slightly overlapping sections 16a and 16b. This arrangement facilitates the peeling of the release liner 16 from the adhesive layer 14 immediately before use.

FIG. 3 also depicts a reinforcing layer 26 that may preferably be adhered to the adhesive layer 14. It may be preferred that the reinforcing layer 26 be attached to the wound closure 10 only in the wound bridging portion 22, more preferably the neck 23, in which case the end portions 20a and 20b are free of the reinforcing layer 26. It is preferred that the reinforcing layer 26 be firmly attached to the wound closure 10 such that the reinforcing layer 26 does not delaminate from the wound closure 10 when the wound closure stretches. More preferably, the reinforcing layer 26 does not delaminate from the wound closure 10 when the wound closure stretches 30%. In the depicted embodiment, the reinforcing layer 26 is attached to the wound closure using the adhesive 14, although the reinforcing layer 26 may be attached to the wound closure 26 using any suitable technique, e.g., adhesive (the same or different than the adhesive used to attach the wound closure 10 to a patient), welding, etc.

If the reinforcing layer 26 is located on the same side of the wound closure 10 as the adhesive 14, then the materials used in the reinforcing layer 26 must be compatible with contact against wounded skin in addition to the desired elongation and elasticity characteristics.

One advantage of positioning the reinforcing layer 26 on the same side of the wound closure 10 as the adhesive 14 is that the adhesive 14 in the wound bridging portion 22 may be covered by the reinforcing layer 26. Covering the adhesive 14 in that area may prevent the adhesive 14 from adhering to the wound edges and potentially causing problems when the wound closure 10 is removed.

Several polymers are known that meet the stated criteria, and polyester terephthalate film, commercially available as Melinex™ S films from DuPont (Wilmington, Del.), is presently considered preferred. These films are commercially available in thicknesses of 50 microns (0.002 inch) and 36 microns (0.0014 inch), both of which are considered suitable in connection with the present invention. Thicker films may be more likely felt by the patient when placed against the tender wound edges. It may be preferred that the material of the reinforcing layer 26 have a thickness of 75 microns (0.003 inch) or less, more preferably 60 microns (0.0023 inch) or less, and possibly even more preferably 30 microns (0.0012 inch) or less.

Figure 4:
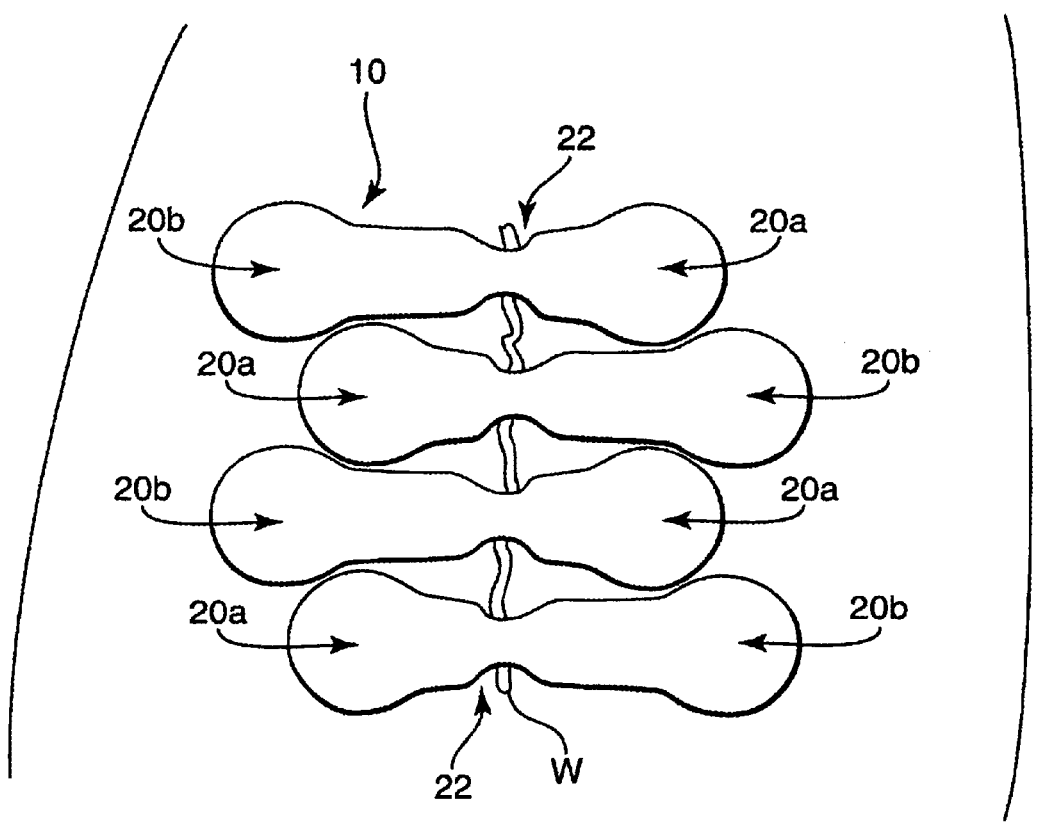
FIG. 4 illustrates four of the wound closures of the present invention used in coordination to hold the wound edges of a wound on the arm of a patient.

Referring now to FIG. 4, four wound closures 10 are used in coordination to hold together the wound edges of a wound (W), illustrated in this case on the arm of a patient. Of particular note is the alternating arrangement of the end portions 20a and 20b, with the long and short end portions 20a and 20b of the wound closures 10 being deployed on opposite sides of the wound alternately. The wider pad portions 24a and 24b may increase the holding power of the wound closures 10, but if the wound closures were end-for-end symmetrical, they might interfere with and overlap each other along a straight wound such as the one depicted. In other words, there would be a limit as to how closely they could be placed together, and that limit might preclude their use if the wound needed to be bound more densely. However, the figure illustrates how the unequal lengths of the end portions 20a and 20b allow the wound closures 10 to nest together for an excellent combination of reduced wound occlusion, sufficient points of binding across the wound per linear wound length, and increased surface area for taking a firm grip on the skin.

Figure 5:
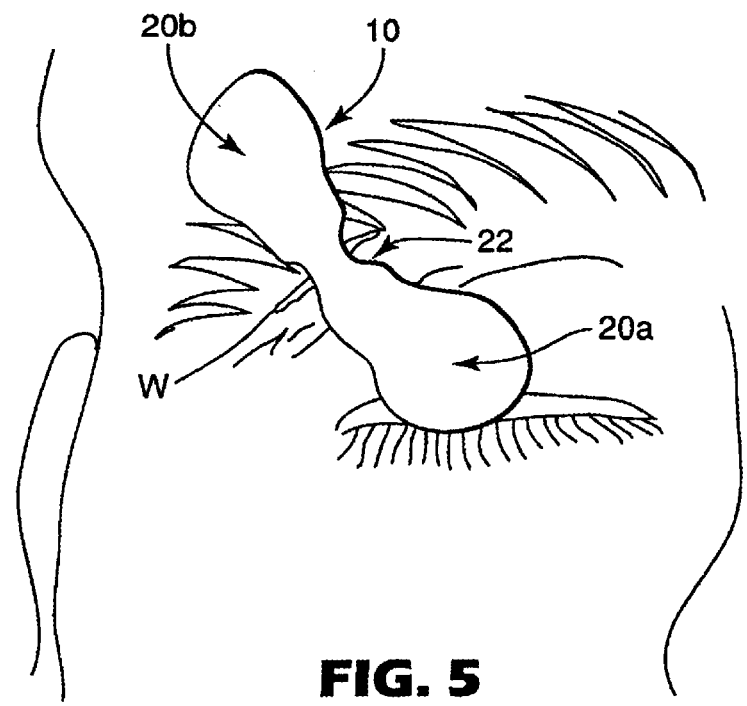
FIG. 5 illustrates a wound closure in use near a closed human eye to bind a wound on the orbital ridge.
Figure 6:
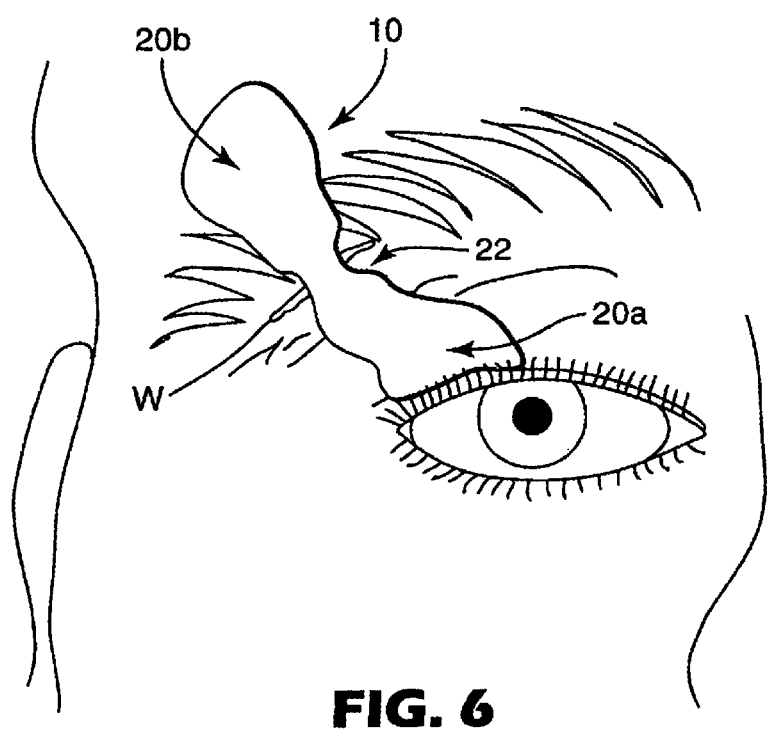
FIG. 6 illustrates the wound closure of FIG. 5 with open eye.

Referring now to FIGS. 5 and 6, a wound closure 10 as described above is illustrated in use near a human eye to bind a wound (W) on the orbital ridge. The short, but wide shape of end portion 20a of the wound closure 10 (including pad portion 24a) offers advantages in closing wounds close to the delicate eye. As depicted in FIG. 6, the elasticity of the wound closure 10 of the present invention is capable of holding the wound closed even under extreme flexing.

Figure 7:
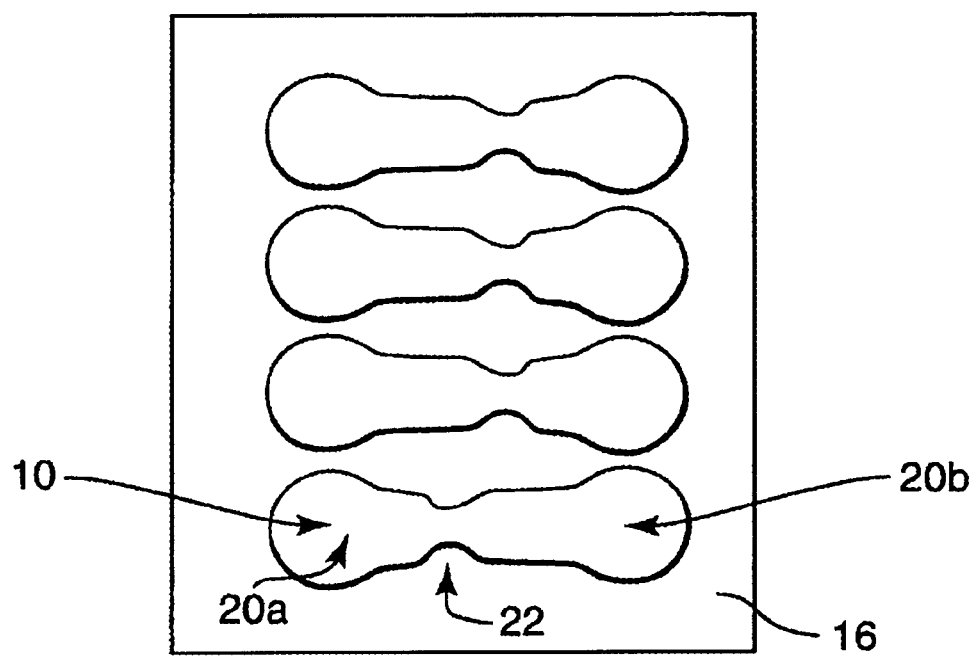
FIG. 7 illustrates four wound closures provided on a single release liner.

Referring now to FIG. 7, one preferred physical form for delivering the wound closures is illustrated. Four (or some other number the consumer finds convenient) wound closures 10 are provided on a single release liner 16. The release liner 16 is large enough and stiff enough to provide a convenient way to hold the wound closures and allows them to be peeled off individually for application to a wound.

Various elastomeric webs are suitable for use as backings 12 in wound closures 10 of the present invention; for example, thin layers of polyvinyl chloride foams may provide the desired properties. Certain nonwoven elastomeric webs based on melt blown webs of thermoplastic elastomeric small diameter fibers may, however, be preferred due to their exceptional conformability and moisture vapor transmission properties. More particularly, elastomeric thermoplastic materials from which microfiber webs can be prepared include, for example, elastomeric polyurethanes, elastomeric polyesters, elastomeric polyamides and elastomeric A-B-A' block copolymers wherein A and A' are styrenic moieties and B is an elastomeric midblock.

The elastomeric small diameter fibers preferred for use with the present invention preferably have diameters of from about 1 micron to greater than 50 microns, more preferably from about 5 microns to about 30 microns. The elastomeric web thus formed may preferably recover at least 85%, more preferably at least 90%, and most preferably at least 95%, in the machine direction after being stretched 30%. It may also be preferred that the web used for the backings 12 recover at least 80%, more preferably at least 85%, most preferably at least 90%, in the cross direction (i.e., transverse to the machine direction) after being stretched 30% in that direction.

Nonwoven melt blown elastomeric webs can be prepared by a process similar to that taught in Wente, Van A., "Superfine Thermoplastic Fibers" in Industrial Engineering Chemistry, Vol.48, pages 1342 et seq. (1965), or in Report No. 4364 of the Naval Research Laboratories, published May 25, 1954 entitled "Manufacture of Superfine Organic Fibers" by Wente, Van A., Boone, C. D. and Fluharty, E. L. (except that a drilled die may preferably be used). The thermoplastic elastomeric materials are extruded through the die into a high velocity stream of heated air which draws out and attenuates the fibers prior to their solidification and collection. The fibers are collected in a random fashion, such as on a perforated screen cylinder, prior to complete fiber solidification so that the fibers are able to bond to one another and form a coherent web which does not require additional binders. The blown fibers can be collected directly on an adhesive film carried on a release liner. Specific physical characteristics of the web are achieved by properly balancing the polymer rheology, the fiber forming and collection phases of the process to achieve desired web properties. More information about elastomeric webs suitable for use with the present invention can be found in co-assigned U.S. Pat. No. 5,230,701 (Meyer et al.), which is hereby incorporated by reference in its entirety.

Suitable backings can also be formed from breathable nonwoven tape backings where the nonwoven tape backing includes a fibrous nonwoven web formed in part by multi-component fibers having an adhesive component region. The multicomponent fibers are distributed throughout the width dimension of the nonwoven tape backing such that adhesive component region is exposed on both outer faces of the nonwoven tape backing. The adhesive component region is preferably a pressure-sensitive adhesive region formed by hot melt coextrusion of the adhesive component and at least one nonadhesive component to form the multicomponent fibers. The nonwoven tape backing is preferably formed simultaneously with the formation of the multicomponent fibers or simultaneously with the collection of the multicomponent fibers into the nonwoven backing. Details about how such materials can be formed and then provided with an adhesive layer may be found in co-assigned U.S. Pat. No. 6,107,219 (Joseph et al.), which is hereby incorporated by reference in its entirety.

The backing 12 is preferably coated with a skin compatible pressure sensitive adhesive layer 14. When multicomponent fiber backings as described above are used for the backing, it may be particularly convenient to prepare a melt blown microfiber pressure sensitive adhesive web and then laminate this web to the backing. The examples entitled "Adhesive Sample" 1, 2, and 3 in U.S. Pat. No. 6,107,219 (Joseph et al.) disclose materials and methods that may be suitable for use with the present invention.

Other preferred pressure sensitive adhesives which can be used in the adhesive layer of the present invention are the normal adhesives which are applied to the skin such as the acrylate copolymers described in U.S. Pat. No. RE 24,906, (which is hereby incorporated by reference in its entirety), particularly a 97:3 weight ratio iso-octyl acrylate:acrylamide copolymer or a 96:4 weight ratio iso-octyl acrylate:acrylamide copolymer. Other medical grade skin adhesives such as copolymers of iso-octyl acrylate and N-vinyl pyrrolidone, or copolymers of iso-octyl acrylate and acrylic acid, can also be used. A layer of about twenty-five grams of skin compatible pressure sensitive adhesive per square meter of integrated backing may be considered suitable.

Liners which are suitable for use in connection with the wound closures of the present invention can be made of kraft papers, polyethylene, polypropylene, polyester or composites of any of these materials. The liners may preferably be coated with release agents such as fluorochemicals or silicones. For example, U.S. Pat. No. 4,472,480, the disclosure of which is hereby incorporated by reference in its entirety, describes low surface energy perfluorochemical liners. Some preferred liners are papers, polyolefin films, or polyester films coated with silicone release materials. One example of a commercially available release liner that may be considered suitable for use with the present invention is a silicone coated release paper available as SC 50 1F M4D from Sopal France, of Dax, France. Also considered suitable is ESP-48 liner, commercially available from DCP-Lohja of Cullman, Ala.

Other combinations of adhesives and liners are contemplated for use with embodiments according to the present invention. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the Handbook of Pressure Sensitive Adhesive Technology, Van Nostrand-Reinhold, 1982, pp. 384–403. U.S. Pat. No. 4,472,480 also describes considerations pertinent to the selection of a perfluoropolyether release liner.

The wound closures according to the present invention may be conveniently made by preparing the backing as a long, indefinite length web which is slit to widths appropriate to the closure to the made. The adhesive layer may then be applied by any suitable technique, e.g., curtain or knife coating. Where desired, a narrow ribbon of material is laid down onto the adhesive layer to form the reinforcing layer. Typically, a release liner is laminated to this construction, either in a single layer or in an overlapped two-piece arrangement as desired. Wound closures are then die cut from the laminated construction, piercing the release liner if individual closures are desired, or sparing the release liner if an arrangement according to FIG. 7 is desired. Conventional slitting and die cutting techniques will serve in a fashion well known to the artisan.

EXAMPLES

The following examples have been selected merely to further illustrate features, advantages, and other details of the invention. It is to be expressly understood, however, that while the examples serve this purpose, the particular materials and components used, as well as other conditions and details, are not to be construed in a manner that would unduly limit the scope of this invention.

Example 1

A backing of blown microfiber web including 3-layer fibers containing 80% polyurethane and 20% "KRATON" PSA/polyethylene blend was laminated to blown microfiber polyacrylate PSA web using the materials and methods described Example 3 of U.S. Pat. No. 6,107,219 (Joseph et al.). A 12.5 mm (0.5 inch) wide strip of Melinex™ S polyester terephthalate film, 36 microns (0.00142 inch) thick (available from DuPont, Wilmington, Del.) was laminated to the polyacrylate PSA web.

A wound closure having an overall length of 57.2 mm (2.25 inch) was die cut from the adhesive composite web thus formed. The wound closure was shaped generally as depicted in the figures, except that the opposing end portions of the wound closure were of equal lengths as measured from the wound bridging portion. The main width of the wound closure was 8 mm, expanding at the ends into pad portions of generally circular shape having a diameter of 12.5 mm (0.5 inch). A neck portion was present within the area containing the polyester film, narrowing to 4 mm wide at its narrowest point.

Example 2

The wound closure according to Example 1 was tested for elongation, adhesion, and recovery after stretch. The wound closure was adhered to a very stretchable and recoverable test substrate which was stretched to force the wound closure to elongate by 30%. Film to be used as the test substrate was made according to the first two paragraphs of Example 1 of U.S. Pat. No. 5,531,855 (Heinecke et al.), which is hereby incorporated by reference in its entirety.

A strip of the test substrate material was attached to two handles so as to leave an unstretched 70 mm span of test substrate between the handles. The wound closure was adhered to the test substrate using its own adhesive layer to the plain side of the test substrate with the long axis of the wound closure aligned with the direction of pull between the handles.

Over the course of approximately two seconds, the handles were pulled sufficiently to force the wound closure to extend to 74.4 mm (30% elongation) in length. A measurement of the elongation of the wound bridging portion was taken, then the force on the handles was gently removed and more measurements taken.

During the time the wound closure was stretched to 30% elongation, the wound bridging portion elongated from 12.5 mm to 13.25 mm, or 6%. After stretching, the wound closure recovered to a length of 58.5 mm (92.4% recovery), and the wound bridging portion recovered to a length of 12.5 mm (essentially 100% recovery).

Alternative shapes for wound closures manufactured according to the present invention can also be found in U.S. Design Pat. Nos. D-461007; D-465572; D-458371; D-457629; and D-457241; all of which are titled SKIN WOUND CLOSURE, filed on even date herewith. All of these documents are incorporated by reference in their entirety.

Various modifications and alterations of the present invention will be apparent to those skilled in the art without departing from the scope of this invention, and it should be understood that this invention is not limited to the illustrative embodiments set forth herein.

What is claimed is:

1. A wound closure for closing a wound in skin, the wound closure comprising:
   an adhesive for adhering the wound closure to skin;
   opposing elastomeric end portions; and
   a wound bridging portion between the end portions;
   wherein the wound closure recovers at least 85% after being stretched 30%, and wherein the wound bridging portion stretches less than the end portions when subjected to the same force, whereby the wound bridging portion tends to maintain the wound closed against forces generated by stretching of skin.

2. The wound closure according to claim 1, wherein the wound bridging portion stretches 8% or less when the wound closure stretches 30%.

3. The wound closure according to claim 1, wherein the wound bridging portion recovers 100% after the wound closure recovers at least 85% after stretching 30%.

4. The wound closure according to claim 1, wherein the wound closure recovers at least 95% after being stretched 30%, and wherein the wound bridging portion stretches 5% or less when the wound closure stretches 30%.

5. The wound closure according to claim 4, wherein the wound bridging portion stretches 1% or less when the wound closure stretches 30%.

6. The wound closure according to claim 1, wherein the wound closure has a length and width, the wound bridging portion comprising a neck having a width less than the width of the end portions.

7. The wound closure according to claim 1, wherein the end portions have unequal lengths as measured from the wound bridging portion to the ends of the wound closure.

8. The wound closure according to claim 1, wherein the adhesive comprises a pressure sensitive adhesive layer, and further wherein any of the pressure sensitive adhesive in the wound bridging portion is covered.

9. A wound closure for closing a wound in skin, the wound closure comprising:
   opposing end portions and an intermediate portion separating the end portions; and
   an adhesive for adhering the wound closure to skin;
   wherein the end portions and the intermediate portion comprise an elastomeric backing;
   and wherein a reinforcing layer is attached to the backing only in the intermediate portion such that the intermediate portion defines a wound bridging portion comprising the elastomeric backing and the reinforcing layer;
   and further wherein the wound closure recovers at least 85% after being stretched 30% and the wound bridging portion stretches less than the end portions when subjected to the same force, whereby the wound bridging portion tends to maintain the wound closed against forces generated by stretching of skin.

10. The wound closure according to claim 9, wherein the wound bridging portion stretches 8% or less when the wound closures stretches 30%.

11. The wound closure according to claim 9, wherein the wound closure recovers at least 95% after being stretched 30%, and wherein the wound bridging portion stretches 5% or less when the wound closure stretches 30%.

12. The wound closure according to claim 11, wherein the wound bridging portion stretches 1% or less when the wound closure stretches 30%.

13. The wound closure according to claim 9, wherein the wound bridging portion recovers 100% after the wound closure recovers at least 85% after stretching 30%.

14. The wound closure according to claim 9, wherein the wound closure has a length and width, the wound bridging portion comprising a neck having a width less than the width of the end portions.

15. The wound closure according to claim 9, wherein the end portions have unequal lengths as measured from the wound bridging portion to the ends of the wound closure.

16. The wound closure according to claim 9, wherein the adhesive comprises a pressure sensitive adhesive layer on the end portions for adhering the wound closure to skin, and further wherein the reinforcing layer covers the pressure sensitive adhesive in the wound bridging portion.

17. The wound closure according to claim 9, wherein the reinforcing layer comprises a polymeric film.

18. The wound closure according to claim 17, wherein the polymeric film has a thickness of 75 microns or less.

19. A wound closure for closing a wound in skin, the wound closure comprising:
   an adhesive for adhering the wound closure to skin;
   two opposing end portions located at opposing ends along a length of the wound closure; and
   a wound bridging portion separating the opposing end portions, the wound bridging portion having a width less than a width of the end portions;
   wherein the opposing end portions comprise unequal lengths as measured from the wound bridging portion to the ends of the wound closure.

20. The wound closure according to claim 19, wherein the adhesive comprises a pressure sensitive adhesive layer, and further wherein any of the pressure sensitive adhesive in the wound bridging portion is covered.

21. The wound closure according to claim 19, wherein the end portions and the wound bridging portion comprise an elastomeric backing, and wherein a reinforcing layer is attached to the backing only in the wound bridging portion, such that the wound bridging portion comprises the elastomeric backing and the reinforcing layer.

22. The wound closure according to claim 21, wherein the reinforcing layer comprises a polymeric film.

23. The wound closure according to claim 22, wherein the polymeric film has a thickness of 75 microns or less.

24. A method of tending a wound, comprising:
   providing a wound closure having a short side and a long side, the wound closure comprising:
      an adhesive for adhering the wound closure to skin;
      two opposing end portions located at opposing ends along a length of the wound closure; and
      a wound bridging portion separating the opposing end portions, the wound bridging portion having a width less than a width of the end portions;
      wherein the opposing end portions comprise unequal lengths as measured from the wound bridging portion to the ends of the wound closure, with the shorter end portion comprising the short side of the wound closure and the longer end portion comprising the long side of the wound closure; and
   adhering the wound closure to a patient such that the wound bridging portion spans a wound.

25. The method according to claim 24, wherein at least two wound closures are adhered to the patient, and wherein the short side of a first wound closure is located on the same side of the wound as the long side of a second wound closure.

26. The method according to claim 24, wherein the wound closure recovers at least 85% after being stretched 30%, and wherein the wound bridging portion stretches less than the end portions when subjected to the same force, whereby the wound bridging portion tends to maintain the wound closed against forces generated by stretching of skin.

27. The method according to claim 26, wherein the wound bridging portion stretches 8% or less when the wound closure stretches 30%.

28. The method according to claim 26, wherein the wound bridging portion recovers 100% after the wound closure recovers at least 85% after stretching 30%.

29. The method according to claim 26, wherein the wound closure recovers at least 95% after being stretched 30%, and wherein the wound bridging portion stretches 5% or less when the wound closure stretches 30%.

30. The method according to claim 29, wherein the wound bridging portion stretches 1% or less when the wound closure stretches 30%.

* * * * *

UNITED STATES PATENT AND TRADEMARK OFFICE
CERTIFICATE OF CORRECTION

| | | |
|---|---|---|
| PATENT NO. | : 7,066,182 B1 | |
| APPLICATION NO. | : 09/671129 | |
| DATED | : June 27, 2006 | |
| INVENTOR(S) | : Wayne K. Dunshee | |

It is certified that error appears in the above-identified patent and that said Letters Patent is hereby corrected as shown below:

On Title Page
Item 56
Under U.S. PATENT DOCUMENTS please add:
--3,568,675    3/09/1971    Harvey
3,824,998    7/23/1974    Snyder
4,726,989    2/23/1988    Mrozinski
5,254,132    10/19/1993    Barley et al.
5,480,935    1/2/1996    Greff et al.
5,753,699    5/19/1998    Greff et al.
6,214,332 B1    4/10/2001    Askill et al.
6,383,502 B1    5/7/2002    Dunshee et al.--

Title Page
Item [56], References Cited, FOREIGN PATENT DOCUMENTS, after "WO 92/10983" insert -- A1 --.
Item [56], References Cited, FOREIGN PATENT DOCUMENTS, after "WO 93/17633" insert -- A1 --.

Item 56
Under FOREIGN PATENT DOCUMENTS please add:
WO 98/26719    A1    6/25/1998
WO 00/06213    A1    2/10/2000
WO 00/56280    A1    9/28/2000
WO 02/26181    A1    4/04/2002

Item [56], References Cited, OTHER PUBLICATIONS, delete "pgs" and insert -- pgs. --, therefore.
Item [56], References Cited, OTHER PUBLICATIONS, delete "jnj gateway" and insert -- jnjgateway. --, therefore.

UNITED STATES PATENT AND TRADEMARK OFFICE
CERTIFICATE OF CORRECTION

PATENT NO. : 7,066,182 B1
APPLICATION NO. : 09/671129
DATED : June 27, 2006
INVENTOR(S) : Wayne K. Dunshee It is certified that error appears in the above-identified patent and that said Letters Patent is hereby corrected as shown below:

Item [56], References Cited, OTHER PUBLICATIONS, insert -- Satas; "Handbook of Pressure-Sensitive Adhesive Technology"; Chapter 18 – Silicone Release Coatings; 1982; Title page, publication page, table of contents; pp. 384-403. --

Signed and Sealed this

Eighteenth Day of September, 2007

JON W. DUDAS
*Director of the United States Patent and Trademark Office*